(12) United States Patent
Kogure et al.

(10) Patent No.: US 11,096,589 B2
(45) Date of Patent: Aug. 24, 2021

(54) BIO-INFORMATION OUTPUT DEVICE, BIO-INFORMATION OUTPUT METHOD AND PROGRAM

(71) Applicant: PARAMOUNT BED CO., LTD., Tokyo (JP)

(72) Inventors: Takamasa Kogure, Tokyo (JP); Toshihide Shiino, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 310 days.

(21) Appl. No.: 15/757,484

(22) PCT Filed: Sep. 2, 2016

(86) PCT No.: PCT/JP2016/075768
§ 371 (c)(1),
(2) Date: Mar. 5, 2018

(87) PCT Pub. No.: WO2017/038966
PCT Pub. Date: Mar. 9, 2017

(65) Prior Publication Data
US 2018/0256036 A1 Sep. 13, 2018

(30) Foreign Application Priority Data

Sep. 4, 2015 (JP) .............................. JP2015-175002
Sep. 1, 2016 (JP) .............................. JP2016-171167

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0245* (2013.01); *A61B 5/113* (2013.01);
(Continued)

(58) Field of Classification Search
CPC . A61B 5/0205; A61B 5/0816; A61B 5/02055; A61B 5/021; A61B 5/4812; G06F 19/3418
See application file for complete search history.

(56) References Cited

U.S. PATENT DOCUMENTS

2011/0068935 A1* 3/2011 Riley ................. A61B 5/02055 340/575
2011/0112442 A1* 5/2011 Meger .................. A61B 5/0002 600/595

(Continued)

FOREIGN PATENT DOCUMENTS

EP 3 005 940 4/2016
JP 7-284482 10/1995
(Continued)

OTHER PUBLICATIONS

International Search Report dated Nov. 22, 2016 in International (PCT) Application No. PCT/JP2016/075768.
(Continued)

*Primary Examiner* — Mohamed Charioui
*Assistant Examiner* — Christine Y Liao
(74) *Attorney, Agent, or Firm* — Wenderoth, Lind & Ponack, L.L.P.

(57) ABSTRACT

The reliability of calculated bio-information of a subject is determined. When the reliability of the bio-information is determined to be high, the bio-information is output, whereas when the reliability of the bio-information is determined to be low, the bio-information is not output. Thus, among the calculated bio-information, only the bio-information of high reliability may be output, or distinctive display may be performed depending on the reliability, whereby it is possible to provide a bio-information output (Continued)

device and the like capable of easily determining bio-information of high reliability.

16 Claims, 5 Drawing Sheets

(51) Int. Cl.
    *A61B 5/0245*     (2006.01)
    *A61B 5/113*     (2006.01)
    *A61B 5/08*     (2006.01)
    *A61B 5/11*     (2006.01)

(52) U.S. Cl.
    CPC ............ *A61B 5/6892* (2013.01); *A61B 5/746* (2013.01); *A61B 5/0816* (2013.01); *A61B 5/1115* (2013.01); *A61B 5/6891* (2013.01)

(56) References Cited

U.S. PATENT DOCUMENTS

| | | |
|---|---|---|
| 2012/0029298 A1 | 2/2012 | Fu et al. |
| 2013/0197382 A1* | 8/2013 | Yang ........................ A61B 7/00 600/528 |
| 2013/0324873 A1* | 12/2013 | Babaeizadeh ........ A61B 5/4848 600/532 |
| 2016/0081630 A1 | 3/2016 | Aoshima |
| 2016/0302736 A1* | 10/2016 | Koyama ................. A61B 5/721 |

FOREIGN PATENT DOCUMENTS

| | | |
|---|---|---|
| JP | H10-314128 | 12/1998 |
| JP | 2006-43445 A | 2/2006 |
| JP | 2008-142162 | 6/2008 |
| JP | 2009-89829 A | 4/2009 |
| JP | 2009-261419 A | 11/2009 |
| JP | 2011-206285 | 10/2011 |
| JP | 2015-12948 | 1/2015 |
| WO | 2005/048832 | 6/2005 |
| WO | 2013/086564 | 6/2013 |
| WO | 2014/196119 | 12/2014 |

OTHER PUBLICATIONS

International Preliminary Report on Patentability dated Mar. 6, 2018 in International (PCT) Application No. PCT/JP2016/075768.

* cited by examiner

BIO-INFORMATION OUTPUT DEVICE, BIO-INFORMATION OUTPUT METHOD AND PROGRAM

TECHNICAL FIELD

The present invention relates to a bio-information output device and the like.

BACKGROUND ART

Various devices have been known to display and record bio-information such as heart rate and respiratory rate of a patient who is a person to be measured. For example, electrocardiographs and respiration examination devices of wearable types to be worn by a patient and those of non-wearable types which perform measurement based on vibration or the like have been known.

Among these, in order to display more accurate bio-information to be measured, there have been known inventions (for example, refer to Patent Document 1 and Patent Document 2), in which noise is removed from the measurement data in a certain interval based on a certain index so as to calculate the numerical value of bio-information in that interval based on the measurement data after noise removal. However, the reliability of the calculated numerical value thus calculated is ambiguous so that many data with low reliability may also be included.

PRIOR ART DOCUMENTS

Patent Documents

Patent Document 1:
    Japanese Patent Application Laid-Open No. 2011-206285
Patent Document 2:
    Japanese Patent Application Laid-Open No. Hei 7-284482

SUMMARY OF THE INVENTION

Problem to be Solved

Conventionally, for the calculated bio-information (respiratory rate, heart rate, etc.), measurements are all displayed whether the reliability of measurement is high or low, except when excessive noise is mixed in the measurement data due to a large body motion or device detachment, or when the input signal is extremely low. For example, also in the patent documents mentioned above, since the calculated bio-information is displayed without its reliability being examined, it has not been known how much degree the displayed bio-information is reliable. Furthermore, there are many devices which continue to display previous values even after excessive noise is mixed in.

In medical and nursing care scenes and medical studies, display and recording of bio-information with low reliability are not desired but display and recording with high accuracy are demanded, so that it is desirable that incorrect information is not displayed and recorded if possible.

For example, in a hospital, if heart rate or respiratory rate takes an abnormal value, an alarm is given so that the medical staff must rush to the patient. Data with low reliability tends to take anomaly values, and unnecessary alarm (false alarm) increases the burden on the medical staff. In particular, non-wearable devices tend to collect more unreliable data as compared with wearable devices such as electrocardiographs, increasing the burden on the medical staff due to false alarms.

In view of the above-described problems, it is therefore an object of the present invention to provide a bio-information output device or the like that facilitates distinguishment of highly reliable bio-information by outputting bio-information of high reliability alone among the calculated bio-information or by performing distinctive display according to reliability.

Means for Solving the Problem

In view of the above-described problems, a bio-information output device of the present invention includes:
    a biosignal acquiring means for acquiring a biosignal of a subject;
    a bio-information calculating means for calculating bio-information from the acquired biosignal;
    a reliability determining means for determining a reliability of the calculated bio-information; and
    a bio-information output means that outputs the bio-information when the reliability is determined to be high by the reliability determining means and does not output the bio-information when the reliability is determined to be low.

A bio-information output device of the present invention includes:
    a biosignal acquiring means for acquiring a biosignal of a subject;
    a reliability determining means for determining the reliability of the bio-information calculated by bio-information calculating means; and a bio-information output means that outputs information on the reliability determined by the reliability determining means as reliability information together with the bio-information.

A bio-information output method of the present invention includes:
    a biosignal acquiring step of acquiring a biosignal of a subject;
    a reliability determining step of determining a reliability of the bio-information by the bio-information calculating means; and
    a bio-information output step of outputting the bio-information when the reliability is determined to be high at the reliability determining step and not outputting the bio-information when the reliability is determined to be low.

Advantages of the Invention

According to the present invention, the bio-information is calculated from the biosignal of the subject. The reliability of the calculated bio-information is determined, and when the reliability is determined to be high by the reliability determining means, the bio-information is output. When the reliability is determined to be low, the bio-information will not be output. As a result, the user using the bio-information can use only highly reliable bio-information.

Further, the bio-information may be added with information on reliability as reliability information and output. This not only enables the user to use highly reliable bio-information, but also use it if desired even if the reliability is low. Thus, it is possible to use the bio-information in accordance with the degree of reliability.

BRIEF DESCRIPTION OF DRAWINGS

FIG. 4(*a*) An example of screen display in the first embodiment.

FIG. 4(*b*) An example of screen display in the first embodiment.

MODE FOR CARRYING OUT THE INVENTION

Now, the best mode for carrying out the invention will be described with reference to the drawings. Specifically, a bio-information output system to which the bio-information output device of the present invention is applied will be described, but the scope to which the present invention is applied is not limited to the embodiment.

1. First Embodiment 1.1 Overall System

Figure 1:
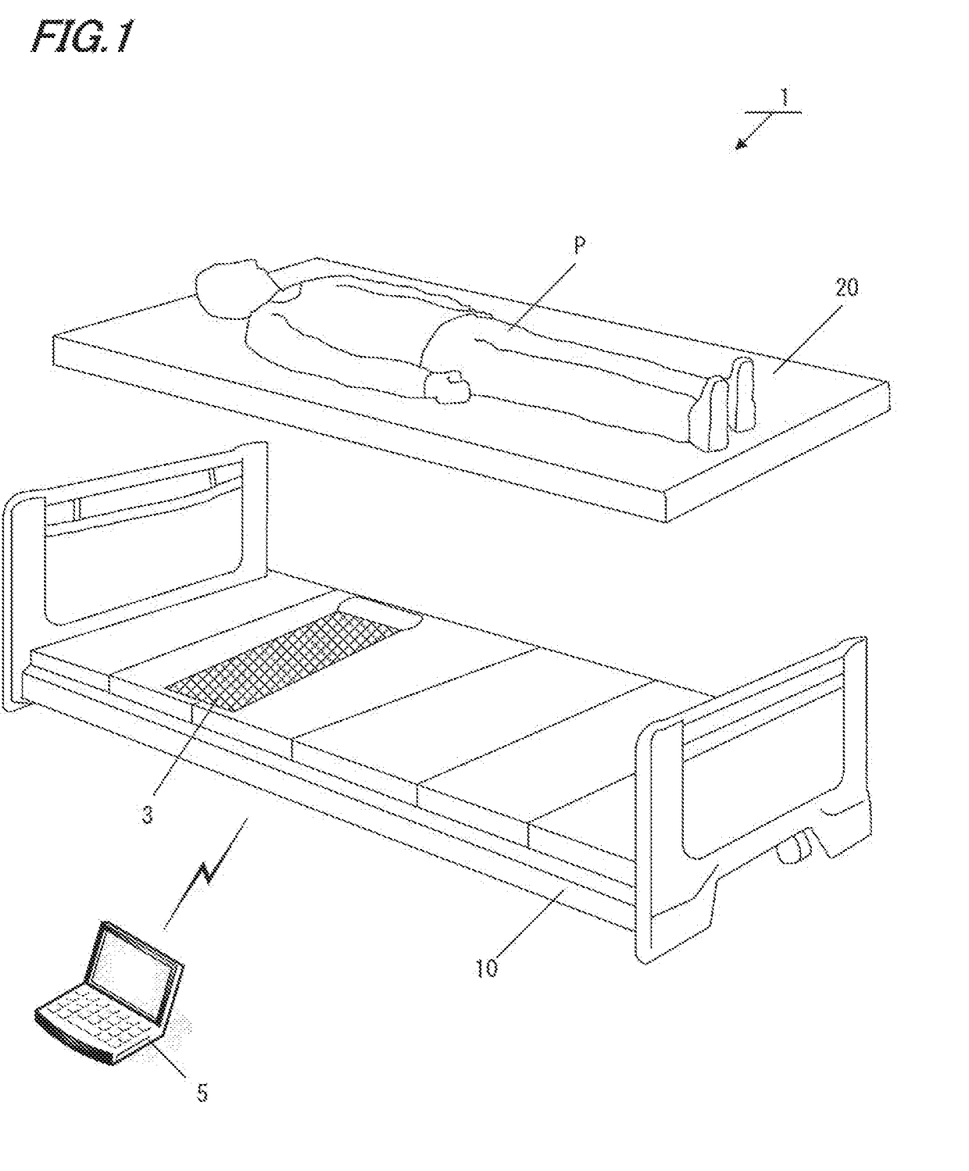
FIG. 1 A diagram for explaining the overall configuration of a first embodiment.

FIG. 1 is a diagram for explaining the overall outline of a bio-information output system 1. As shown in FIG. 1, the bio-information output system 1 includes a detection device 3 placed between a floor portion of a bed 10 and a mattress 20, and a processing device 5 for processing output values from the detection device 3. The detection device 3 and the processing device 5 constitute a bio-information output device.

When a subject to be measured as to bio-information (hereinafter referred to as "patient P") resides on the mattress 20, the detection device 3 detects the body motion (vibration) as the biosignal of the patient P via the mattress 20. Then, based on the detected vibration, the bio-information of the patient P is calculated. In the present embodiment, it is possible to output and display the calculated bio-information (for example, respiratory rate, heart rate) as bio-information of the patient P. For example, the detection device 3 may be integrally formed by providing a storage unit, a display unit and the like. Further, since the processing device 5 may employ a general-purpose device, the processing device is not limited to information processing devices such as computers and the like, but can be constituted of a device such as a tablet device and a smartphone, for example.

Also, the subject may be a person who is under medical treatment or needs care. Healthy persons who do not need nursing care, elder people, children, disabled people and even animals may be handled.

Here, the detection device 3 is shaped sheet-like so as to reduce its thickness. Thereby, even if the detection device is set between the bed 10 and the mattress 20, it can be used without causing the patient P to feel uncomfortable.

It should be noted that the detection device 3 only needs to acquire biosignals (such as body motion, respiratory motion, ballistocardiographic motion, etc.) of the patient P. Though in the present embodiment, the body motion is used to acquire and calculate the heart rate and the respiratory rate, it is possible, for example, to detect the body motion of the patient P by using an infrared sensor, based on the acquired image, etc., or using an actuator with a strain gauge.

1.2 Functional Configuration

Figure 2:
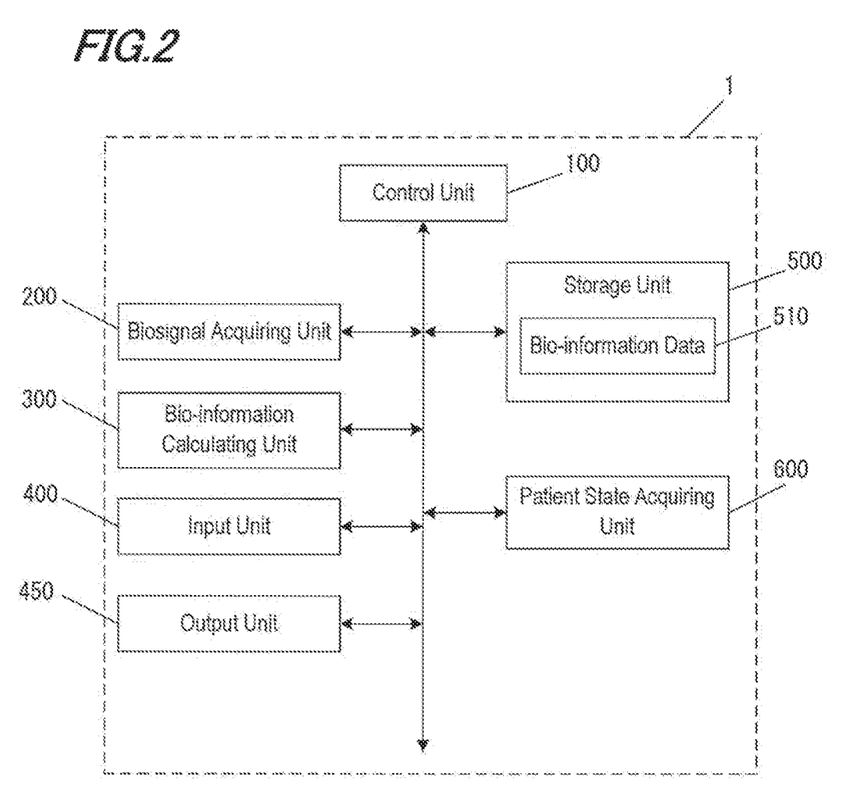
FIG. 2 A diagram for explaining a functional configuration in the first embodiment.

Subsequently, the functional configuration of the bio-information output system 1 (bio-information output device) will be described with reference to FIG. 2. The bio-information output system 1 in the present embodiment includes the detection device 3 and the processing device 5, and each functional unit (process) other than a biosignal acquiring unit 200, may be realized by either of them.

The bio-information output system 1 includes a control unit 100, the biosignal acquiring unit 200, a bio-information calculating unit 300, an input unit 400, an output unit 450, a storage unit 500 and a patient state acquiring unit 600. In the case of FIG. 1, the control unit 100, the biosignal acquiring unit 200 and the storage unit 500 are provided in the detection device 3 while the control unit 100, the bio-information calculating unit 300, the input unit 400, the output unit 450 and the storage unit 500 are provided in the processing device 5. On the other hand, the patient state acquiring unit 600 may use the biosignal acquiring unit 200 or may be provided separately in the bed 10.

The control unit 100 is a functional unit for controlling the operation of the bio-information output system 1 and is configured of control circuits necessary for the bio-information output system 1 such as a CPU and others. The control unit 100 reads out and runs various programs stored in the storage unit 500 to realize various processes. In the present embodiment, the control unit 100 operates as a whole, but it is provided separately in the detection device 3 and the processing device 5.

The biosignal acquiring unit 200 is a functional unit for acquiring biosignals of the patient P. In the present embodiment, as one example a sensor for detecting body motion of the patient P is used to acquire the body motion which is a kind of a biosignal. Then, the acquired body motion is output as body motion data. Based on this body motion data, various bio-information of the patient P can be calculated. Further, based on the body motion data, it is also possible to grasp the condition of the patient P on the bed (for example, whether or not the patient P is lying on the bed, whether the patient P is staying on the bed, leaving the bed or sitting on the edge of the bed, etc.) and also grasp the sleep state (sleeping, awakening) of the patient.

In the present embodiment, the biosignal acquiring unit 200 acquires the vibration (body motion) of the patient by means of a pressure sensor, for example, and acquires breathing and heartbeat from the vibration. However, a load sensor may be used to detect change of the position of the center of gravity (body motion) of the patient, thereby acquire the biosignal, or a microphone may be provided to acquire bio-information based on the sound picked up by the microphone. Any sensor may be used as long as biosignals of the patient can be obtained.

That is, the biosignal acquiring unit 200 may be connected to a device such as the detection device 3, or it is also possible to provide a configuration that the biosignal acquiring unit 200 receives biosignals from external devices.

The bio-information calculating unit 300 is a functional unit for calculating bio-information (respiratory rate, heart rate, etc.) of the patient P. In the present embodiment, the respiration component/heart rate component may be extracted from the body motion acquired from the biosignal acquiring unit 200 so as to determine the respiratory rate and heart rate based on the respiration interval and heartbeat interval. Alternatively, the periodicity of the body motion may be analyzed (by Fourier transform, etc.), to calculate the respiratory rate and heart rate from the peak frequencies.

The input unit 400 is a functional unit for allowing the measurer to input various conditions and perform operation input for starting measurement. This function is, for example, implemented by hardware keys, software keys or some other input means.

The output unit 450 is a functional unit for outputting the sleep state and bio-information such as heart rate and respiratory rate and notifying anomalies of bio-information. The output unit 450 may be a display device such as a display or a notification device (sound output device) for giving an alarm or the like. Further, it may be an external storage device that stores data, a transmitter that transmits data via a communication path, and the like. Further, it may be a communication device for reporting to other devices.

The storage unit 500 is a functional unit that stores various data and programs for the bio-information output system 1 to operate. The control unit 100 reads out and runs the program stored in the storage unit 500 to realize various functions. Here, the storage unit 500 is composed of, for example, a semiconductor memory, a magnetic disk device and/or the like. In this case, the storage unit 500 stores bio-information data 510.

Stored in the bio-information data 510 are the respiratory rate and heart rate calculated from the acquired biosignal (body motion). Though, in the present embodiment, both the respiratory rate and the heart rate are stored, only one of them may be stored. Further, other information (for example, variations in respiration amplitude) may be stored as long as it is bio-information that can be calculated by the bio-information calculating unit 300.

The patient state acquiring unit 600 is a device for acquiring the state of the patient. For example, a load sensor or the like arranged in the bed 10 is used to grasp the state of the patient (lying on bed, leaving bed, staying in bed, etc.). As described above, the patient state may be acquired based on the biosignal acquired by the biosignal acquiring unit 200.

1.3 Processing Flow

Figure 3:
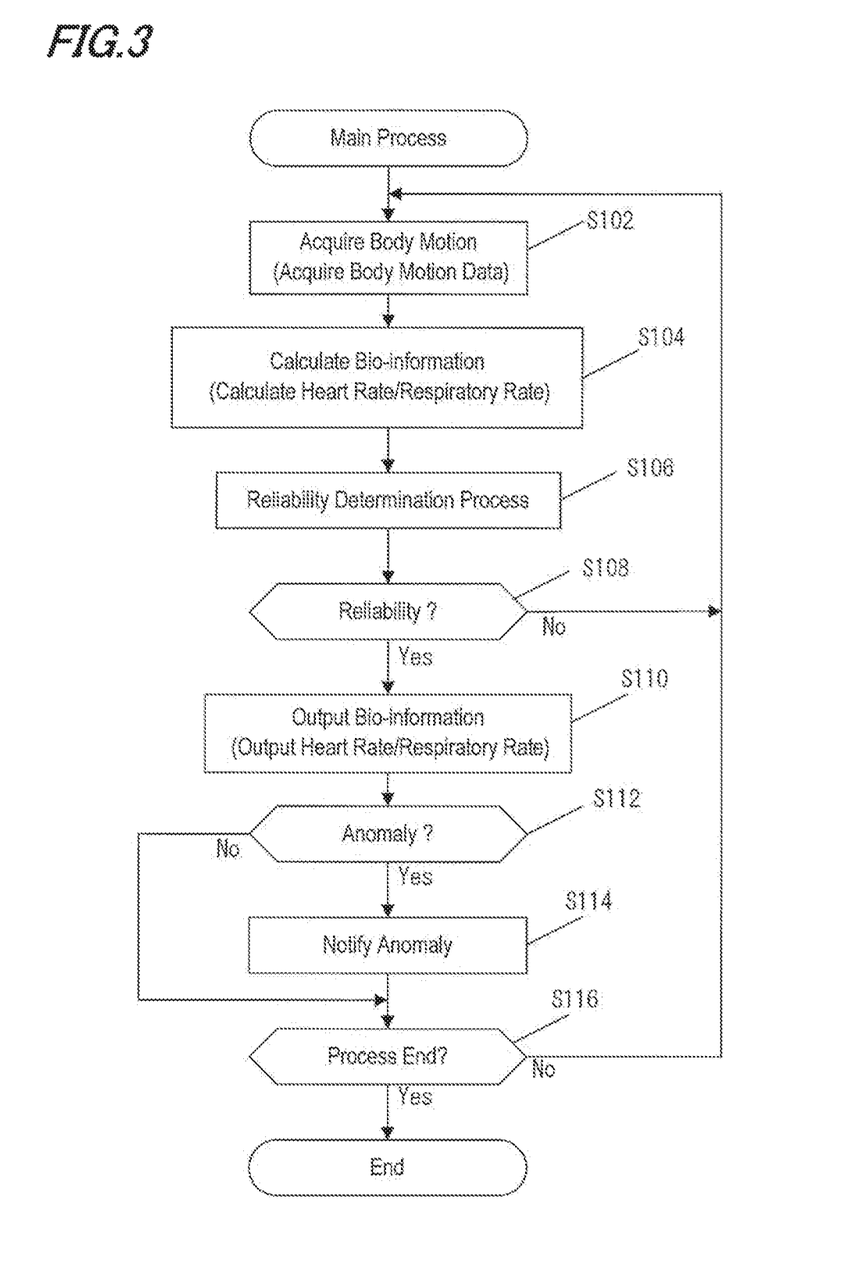
FIG. 3 A processing flow for explaining an operation in the first embodiment.

Subsequently, the flow of the processing of the bio-information output system 1 (bio-information output device) in the present embodiment will be described with reference to FIG. 3. First, body motion is acquired. Specifically, body motion data is acquired as a kind of biosignal from the biosignal acquiring unit 200 (Step S102). As the body motion data, it is possible to acquire it by, for example, detecting vibration.

Subsequently, the bio-information calculating unit 300 calculates bio-information (Step S104). In the present embodiment, the body motion acquired as a biosignal is separated into a respiratory component and a heartbeat component so as to calculate heart rate and respiratory rate as bio-information.

Here, various methods can be considered as methods for calculating heart rate and respiratory rate. For example, the body motion data is filtered so as to extract the respiratory component and determine the breath interval for each breath. Then, the respiratory rate is calculated based on the breath interval. Also, the body motion data is filtered to extract the heart beat component and determine the heart beat interval for each beat. Then, the heart rate is calculated based on the heart beat interval.

Alternatively, calculation may be performed by analyzing the periodicity of the body motion data to find the respiratory rate and the heart rate from the peak frequencies.

Further, in the present embodiment, values calculated on the basis of body motion data, for example every 5 seconds are used. Specifically, calculation is performed every 5 seconds based on the heart rate and/or the respiratory rate calculated during a predetermined period of time. In the present embodiment, both the heart rate and the respiratory rate are calculated, but calculation may be performed for either one of them alone.

Subsequently, a reliability determination process for determining the reliability of the calculated heart rate and respiratory rate is executed (Step S106). Here, as a method of calculating reliability, various methods can be considered, but in this embodiment, for example, one of the following methods is used.

(1) Reliability Evaluation Based on Calculation Conditions:

Reliability evaluation is performed based on calculation conditions for calculating bio-information. For example, when the patient is not in a recumbent state, that is, when the patient is leaving the bed or when the patient is in a sitting position, the patient state acquiring unit 600 determines that the reliability is low. When the bed is connected to an external device such as a bedsore prevention air mat or the like, it is determined that the reliability is low when the external device is generating vibration. That is, in order to evaluate reliability, a state determining means of determining the state of the patient is used.

(2) Reliability Evaluation in Bio-Information Calculation Process:

Reliability is evaluated in the process of calculating bio-information using various criteria. For example, reliability is evaluated to be low when the variation (standard deviation, variation coefficient, etc.) of expiration and inspiration or beat interval is large. Also, reliability is evaluated based on the magnitude and variation of the amplitude of the waveform after filtering. In other words, when there is variation in amplitude, reliability is evaluated to be low.

For example, heartbeat (respiratory) intervals within a short period of time are usually substantially equal. Therefore, when variations in heartbeat (respiratory) intervals are large, it is determined that there is undetection or false detection, and reliability is evaluated to be low.

When a plurality of sensors are provided, reliability is evaluated based on a difference in values calculated from the plurality of sensors. That is, when there are large differences among the plurality of sensors, reliability is evaluated to be low.

Also, when bio-information is calculated by analyzing the periodicity of body motion data, it is possible to evaluate reliability from, for example, the degree of protrusion of peaks in the frequency spectrum and/or the variational of the detection values from the plurality of sensors.

(3) Reliability Evaluation of Calculated Respiratory Rate/Heart Rate:

When the calculated heart rate and respiratory rate greatly deviate from previously calculated values, reliability is evaluated to be low. Examples may include a case where a heart rate value that is greater than twice the value that has been calculated is calculated, a case where the respiratory rate fluctuate beyond its threshold and the like.

Further, an average of the calculated bio-information at the past several times (e.g., five times) may be calculated, and if the current value greatly deviates from the average, or when the inclination (differential value) is steep, it is possible to determine that reliability is low. Further, the output reliability may be graded. When, for example, the current value of bio-information becomes greater than the twice (or smaller than the half) the previously calculated value of bio-information, reliability is evaluated to be considerably low. When, for example, the current value of bio-information falls within a range from 1.5 to 2 times (or ½ to ⅔ times) the previously calculated value of bio-information, reliability is evaluated to be a little low.

When the calculated heart rate and respiratory rate exceed predetermined threshold values or are less than the threshold values, reliability is determined to be low. For example, when the respiratory rate is 0 or 1, or when the heart rate exceeds 200, reliability is determined to be low. The threshold values may be set by the measurer or may be set according to the age and/or health condition of the patient.

In this way, when it is determined that reliability is low, the bio-information, i.e., the heart rate and the respiratory rate are not output (Step S108; No→Step S102). On the other hand, if it is determined that reliability is high, the heart rate and the respiratory rate are output (Step S108; Yes→Step S110). The destination to which the heart rate and respiratory rate are output may be displayed on a screen display as an example of the output unit 450, or may be displayed on another terminal (for example, a tablet, smartphone or the like). Further, the data may be transmitted to a server or a management apparatus or recorded on a recording medium. That is, the heart rate and the respiratory rate are output to anyone of the apparatus, the recording medium, and the transmission destination.

It is determined at this stage whether there is an anomaly in the output heart rate and respiratory rate (Step S112). When it is determined that there is an anomaly, the anomaly is notified (Step S112; Yes→Step S114). Here, "presence of an anomaly" means a state needing a notification to be given to medical staffs, care workers, etc., including cases where the heart rate is higher than a predetermined threshold, where the respiratory rate is lower than a predetermined threshold, where unreliable calculation values have been given frequently in a predetermined interval, and the like.

1.4 Screen Example

Figure 4:
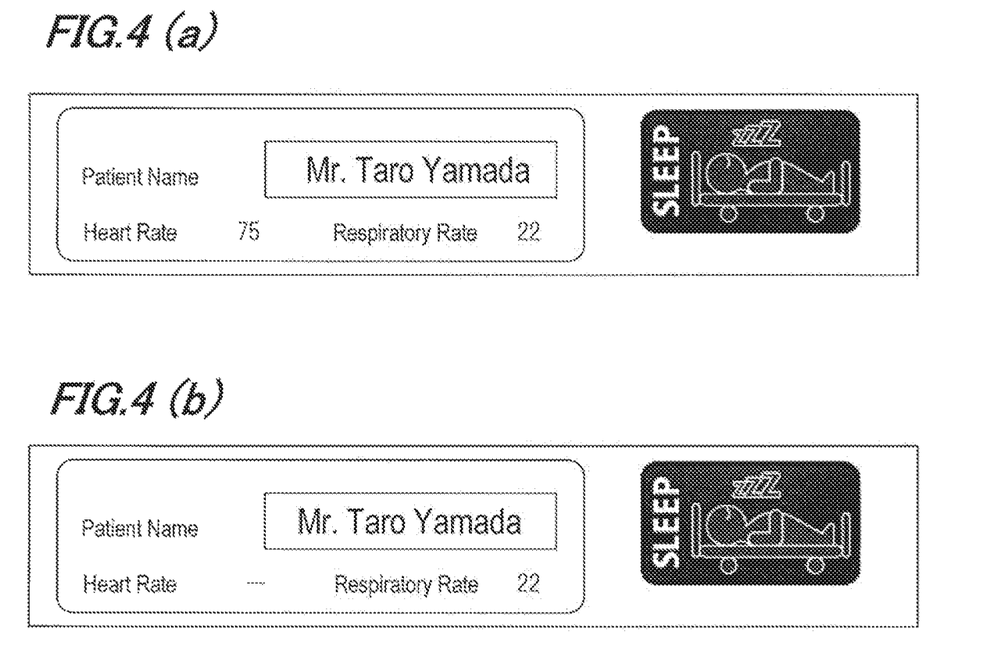

FIG. 4 is shows a screen example when screen display is performed in the output unit 450 in the above-described embodiment. For example, as shown in FIG. 4 (*a*), the patient's name (e.g., "Taro Yamada"), heart rate (e.g., "75"), respiratory rate (e.g., "22") and patient state (e.g., "sleep indicator") are displayed on the screen.

At this time, if it is determined that the reliability of the heart rate is low, the heart rate is not displayed as shown in FIG. 4 (*b*). In the case of FIG. 4 (*b*), the display of "-" enables the staffs and the like to confirm an anomaly state that correct measurement has not been performed.

1.5 Effects

Now, the effects when this embodiment is applied will be described. As an example, heart rate was measured for 20 subjects. Here, as the measurement condition, the measurement time per person was 2 hours 16 minutes on average and the total measurement time was 45 hours 27 minutes. Also, as the instruments for heart rate measurement, a sleeping SCAN (registered trademark) made by Paramount Bed Co. Ltd., which is a non-wearing device that can detect heartbeat by detecting vibration and an electrocardiograph (ECG) that performs measurement with electrodes fitted to the patient body, were used.

Here, the coincidence ratio between the wearing type and the non-wearing type was 98.9% when all data was output regardless of reliability. The measurement ratio was 86.0% (39 hours 6 minutes). In contrast to this, when unreliable data was not output, the coincidence ratio between the wearing type and the non-wearing type was 99.3%. The measurement ratio was 84.9% (38 hours 36 minutes).

In the present study, data was determined to be unreliable when the variation coefficient of the variation in the heartbeat interval for each beat exceeded a certain threshold, specifically, when a variation from the average value of the heart rate every 5 seconds calculated at the last three times became equal to or greater than 40. This effect may seem to be ineffective, but can produce a good effect when it is considered that the heart rate with low reliability is highly likely to take an abnormal value (extremely too high value or too low value). Since this study was carried out in the recumbent state in the laboratory, a more enhanced effect can be expected because various noises that degrade reliability may be mixed in the actual hospital environment.

As described above, according to the present embodiment, the data to be displayed contains a high proportion of data with high accuracy. Therefore, when a staff or the like checks bio-information, it is possible to acquire the correct value. In addition, when a notifying process is performed based on bio-information (respiratory rate, heart rate, etc.), this configuration is effective since unnecessary notice will not be given based on unreliable bio-information.

2. Second Embodiment

Next, a second embodiment will be described. In the first embodiment, description has been made on the assumption that unreliable bio-information is not output. Description in the present embodiment, however, will be made on a case where output is performed even if the reliability is low.

That is, even if it is determined at Step S108 that there is no reliable data, the heart rate and the respiratory rate are output (Step S108→Step S110). That is, when the Step S108 is No, the processing returns to the Step S102. In this embodiment, however, the processing proceeds to the Step S110. At this time, reliability information which is information relating to the reliability determined on the output data is output together. For example, attaching a flag or attaching an additional indication enables the user to easily judge the reliability of the bio-information.

Figure 5:
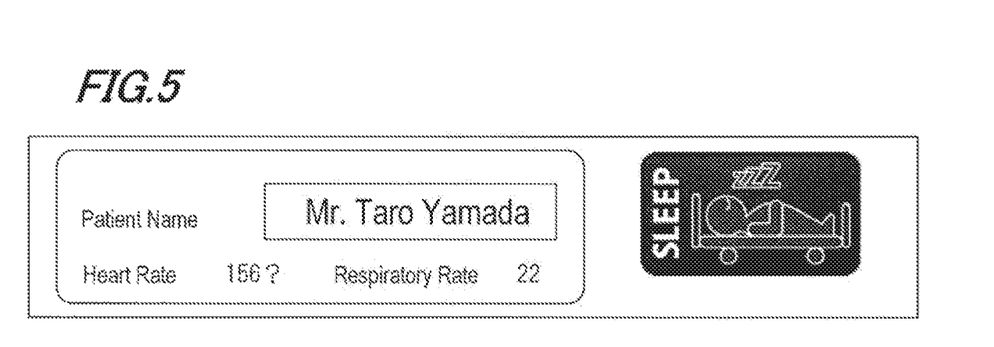
FIG. 5 An example of screen display in a second embodiment.

For example, "?" may be added to the heart rate and displayed, as shown in FIG. 5. This can be done because a "low reliability" flag (reliability information) is attached to the heart rate information, and is displayed based on the flag.

As a result, the user can understand that the value of the heart rate is displayed in a "low reliability" state. Thus, according to the present embodiment, even if data that is determined to have low reliability is output, it is distinctively displayed that reliability is low, whereby the user can appropriately get hold of the patient state.

Further, the display may be changed depending on the reliability information. For example, it is possible to change the display method such that highly reliable bio-information is displayed in black, whereas low reliable bio-information is displayed in gray. Further, in the case where there are a plurality of reliability grades, information on reliability may also be given to the user by changing, for example, the color intensity, the brightness and the color temperature.

As for data with low reliability, it is also possible to perform such a process as not to execute a notifying operation, or not to record the data even if it displayed. More specifically, when it is determined that the data is not reliable at Step S108 (Step S108; No), in this embodiment the processing goes to Step S110. Then, the heart rate and the respiratory rate are output at Step S110, but by not executing the procedures at Step S112 and Step S114, it is possible to realize the process of not performing anomaly notification.

3. Third Embodiment

Figure 6:
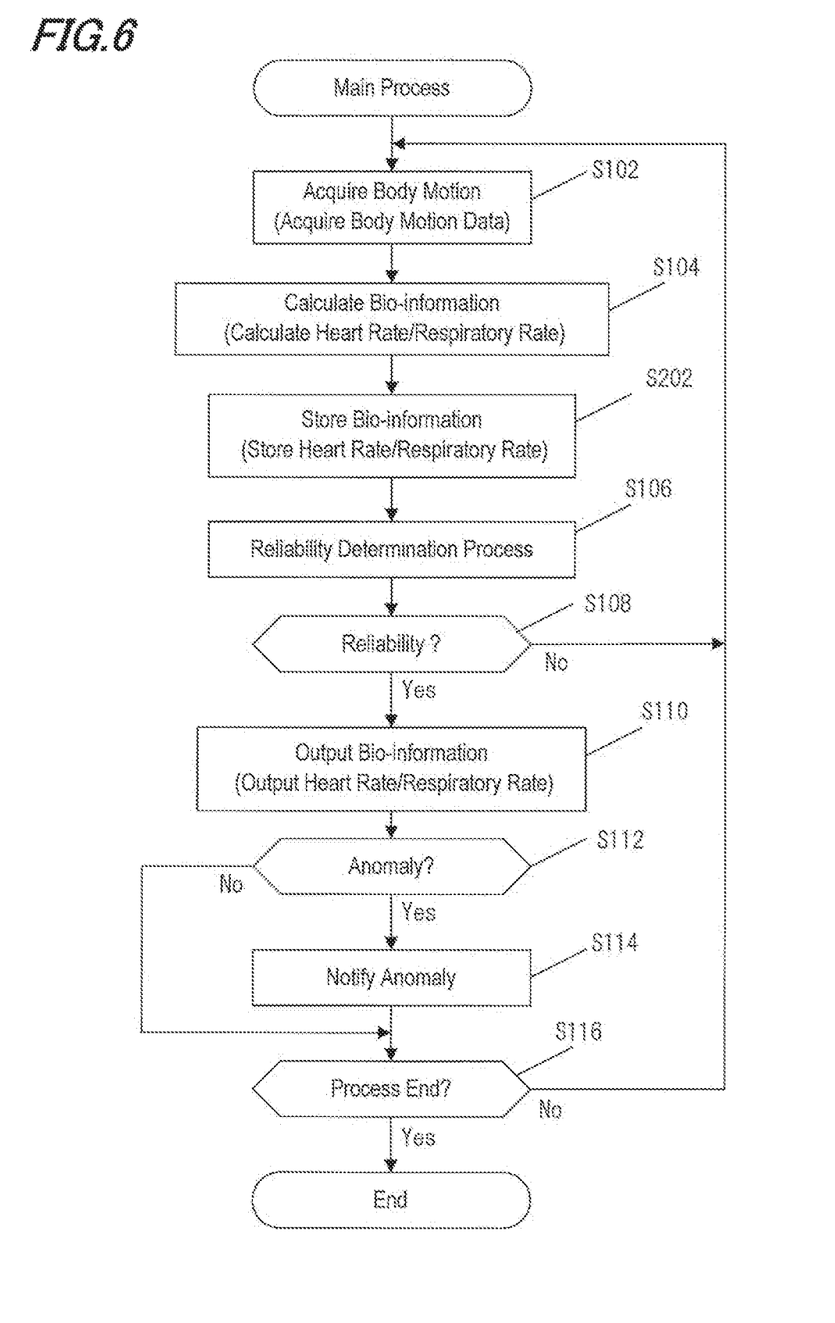
FIG. 6 A processing flow for explaining an operation in a third embodiment.

Subsequently, a third embodiment will be described. The third embodiment is a process of storing bio-information while determining reliability. FIG. 6 shows a processing flow in the third embodiment. The process in FIG. 6 is a replacement of the process of the first embodiment shown in FIG. 3, and the same steps are allotted with the same reference numerals, and the description thereof is omitted.

Specifically, as shown in FIG. 6 the bio-information (for example, heart rate/respiratory rate) calculated at Step S104 is stored in the storage unit 500. Accordingly, the calculated bio-information is stored regardless of the reliability, but reliable bio-information can be output (Step S108; Yes→Step S110).

Here, in the reliability determination process (Step S106), reliability is determined based on the stored bio-information.

Here, Step S202 may be executed after Step S106 or in parallel with Step S106. In this case, the bio-information is stored for use in other processing, and the reliability determining means determines reliability based on the bio-information calculated at Step S104.

4. Variational Examples

Although the embodiments of the present invention have been described in detail with reference to the drawings, the specific configuration should not be limited to the above embodiments. Designs and others that do not depart from the gist of the present invention should also be included in the scope of claims.

Note that the detection device 3 in the above-described embodiments may be one that is simply placed on the mattress 20 to detect the body motion of the patient P. In this case, the system can be realized simply by using, for example a smartphone or the like. That is, the present invention can take any form as long as it can determine the reliability of bio-information based on the biosignal finally obtained and the calculated bio-information.

Further, though description of the present embodiment has been made by using body motion as an example of a biosignal, for example, a temperature (to calculate the respiratory rate by measuring the temperature of nasal breathing), a blood flow (measuring pulses using the light absorption amount) and other biosignals may be used.

As the biosignal/bio-information, for example, signals such as an electroencephalogram, perspiration and the like can be used.

DESCRIPTION OF REFERENCE NUMERALS

1 bio-information output system
3 detection device
5 processing device
10 bed
20 mattress
100 control unit
200 biosignal acquiring unit
300 Bio-information calculating unit
400 input unit
450 output unit
500 storage unit
510 bio-information data
600 patient state acquiring unit

The invention claimed is:

1. A system for determining reliable bio-information comprising:
   a bed;
   a sensor on the bed configured to acquire body motion data of a user;
   control circuitry configured to:
      calculate bio-information of the user from the body motion data,
      determine whether the calculated bio-information is reliable bio-information by analyzing the calculated bio-information with respect to criteria which indicates whether the bio-information is reliable or not reliable, and
      output the calculated bio-information as reliable bio-information when it is determined that the calculated bio-information satisfies the criteria,
      wherein the control circuitry is configured not to output the calculated bio-information when it is determined that the calculated bio-information does not satisfy the criteria, wherein:
      the control circuitry calculates a heart rate and/or a respiratory rate of the user as the bio-information from the body motion data,
      wherein the control circuitry is further configured to output a sign instead of the calculated bio-information when it is determined that the calculated bio-information does not satisfy the criteria.

2. The system according to claim 1, wherein:
   the control circuitry calculates a heartbeat interval and/or a respiration interval of the user as the bio-information from the body motion data, analyzes the bio-information with respect to interval size as the criteria, and determines that the calculated bio-information is reliable bio-information based on whether or not a variation in the interval is large.

3. The system according to claim 1, wherein:
   the control circuitry determines a state of the user, analyzes the bio-information with respect to the state of the user as the criteria, and determines that the calculated bio-information is reliable bio-information based on the state of the user.

4. The system according to claim 3, wherein
   the control circuitry determines, as the state of the user, whether or not the user is in a recumbent state, and determines that the calculated bio-information is not reliable bio-information when the subject is not in the recumbent state.

5. The system according to claim 3, further comprising a load sensor, wherein the control circuitry determines the state of the user based on information from the load sensor.

6. The system according to claim 1, further comprising a memory for storing the calculated bio-information,
   wherein
      the control circuitry reads the stored bio-information so as to determine whether the stored bio-information is reliable bio-information.

7. A method for determining reliable bio-information comprising:
   acquiring with a sensor body motion data of a user on a bed;
   calculating with control circuitry bio-information of the user from the body motion data;

determining with the control circuitry whether the calculated bio-information is reliable bio-information by analyzing the calculated bio-information with respect to criteria which indicates whether the bio-information is reliable or not reliable; and outputting with the control circuitry the calculated bio-information as reliable bio-information when it is determined that the calculated bio-information satisfies the criteria, wherein the calculated bio-information is not output when it is determined that the calculated bio-information does not satisfy the criteria, comprising calculating a heart rate and/or a respiratory rate of the user as the bio-information from the body motion data, wherein the control circuitry is further configured to output a sign instead of the calculated bio-information when it is determined that the calculated bio-information does not satisfy the criteria.

8. The system according to claim 7, comprising calculating a heartbeat interval and/or a respiration interval of the user as the bio-information from the body motion data, analyzing the bio-information with respect to interval size as the criteria, and determining that the calculated bio-information is reliable bio-information based on whether or not a variation in the interval is large.

9. The method according to claim 7, comprising determining a state of the user, analyzing the bio-information with respect to the state of the user as the criteria, and determining that the calculated bio-information is reliable bio-information based on the state of the user.

10. The method according to claim 9, comprising determining, as the state of the user, whether or not the user is in a recumbent state, and determining that the calculated bio-information is not reliable bio-information when the subject is not in the recumbent state.

11. The system according to claim 7, further comprising storing in a memory the calculated bio-information, and reading the stored bio-information so as to determine whether the stored bio-information is reliable bio-information.

12. A non-transitory computer readable medium having stored thereon a program for causing a processor to execute a method for determining reliable bio-information comprising:

acquiring with a sensor body motion data of a user on a bed;

calculating with control circuitry bio-information of the user from the body motion data;

determining with the control circuitry whether the calculated bio-information is reliable bio-information by analyzing the calculated bio-information with respect to criteria which indicates whether the bio-information is reliable or not reliable; and outputting with the control circuitry the calculated bio-information as reliable bio-information when it is determined that the calculated bio-information satisfies the criteria, wherein the control circuitry is configured not to output the calculated bio-information when it is determined that the calculated bio-information does not satisfy the criteria, wherein the method comprises calculating a heart rate and/or a respiratory rate of the user as the bio-information from the body motion data, and wherein the control circuitry is further configured to output a sign instead of the calculated bio-information when it is determined that the calculated bio-information does not satisfy the criteria.

13. The non-transitory computer readable medium according to claim 12, wherein the method comprises, calculating a heartbeat interval and/or a respiration interval of the user as the bio-information from the body motion data, analyzing the bio-information with respect to interval size as the criteria, and determining that the calculated bio-information is reliable bio-information based on whether or not a variation in the interval is large.

14. The non-transitory computer readable medium according to claim 12, wherein the method comprises determining a state of the user, analyzing the bio-information with respect to the state of the user as the criteria, and determining that the calculated bio-information is reliable bio-information based on the state of the user.

15. The non-transitory computer readable medium according to claim 14, wherein the method comprises determining, as the state of the user, whether or not the user is in a recumbent state, and determining that the calculated bio-information is not reliable bio-information when the subject is not in the recumbent state.

16. The system according to claim 12, wherein the method further comprises storing in a memory the calculated bio-information, and reading the stored bio-information so as to determine whether the stored bio-information is reliable bio-information.

* * * * *